(12) United States Patent
Ritchie et al.

(10) Patent No.: US 7,118,564 B2
(45) Date of Patent: Oct. 10, 2006

(54) MEDICAL TREATMENT SYSTEM WITH ENERGY DELIVERY DEVICE FOR LIMITING REUSE

(75) Inventors: Paul G. Ritchie, Loveland, OH (US); Robert Mason Trusty, Cincinnati, OH (US); Jane A. Sheetz, Cincinnati, OH (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 0 days.

(21) Appl. No.: 10/723,799

(22) Filed: Nov. 26, 2003

(65) Prior Publication Data

US 2005/0113815 A1    May 26, 2005

(51) Int. Cl.
*A61B 18/22* (2006.01)
(52) U.S. Cl. ............................................. 606/16; 2/10
(58) Field of Classification Search ................. 128/898; 606/2, 16
See application file for complete search history.

(56) References Cited

U.S. PATENT DOCUMENTS

| | | | |
|---|---|---|---|
| 4,695,697 A | 9/1987 | Kosa | |
| 4,822,997 A | 4/1989 | Fuller et al. | |
| 5,076,653 A * | 12/1991 | Kayashima et al. | ........ 385/109 |
| 5,196,005 A | 3/1993 | Doiron et al. | |
| 5,267,995 A | 12/1993 | Doiron et al. | |
| 5,269,777 A | 12/1993 | Doiron et al. | |
| 5,303,324 A | 4/1994 | Lundahl | |
| 5,337,381 A | 8/1994 | Biswas et al. | |
| 5,363,458 A | 11/1994 | Pan et al. | |
| 5,383,874 A | 1/1995 | Jackson et al. | |
| 5,400,267 A | 3/1995 | Denen et al. | |
| 5,469,524 A | 11/1995 | Esch et al. | |
| 5,487,386 A | 1/1996 | Wakabayashi et al. | |

(Continued)

FOREIGN PATENT DOCUMENTS

EP     0 951 921 A3    3/2000

(Continued)

OTHER PUBLICATIONS

EPO Search Report dated Feb. 18, 2005 for corresponding patent application, European Patent Application No. EP 04 25 7326.

(Continued)

*Primary Examiner*—Henry M Johnson, III (57) ABSTRACT

The present invention provides an energy delivery device for use with a medical treatment system for the more efficacious treatment of patients during laser surgery which limits the number of uses or prevents reuse of the energy delivery device after a certain threshold limit has been reached. The energy delivery device comprises a diffusing optical fiber and a memory device having data programmed therein and being operatively connected to an energy generator the optical fiber includes a temperature sensor for generating a temperature signal in a closed loop manner. The data stored in the memory device includes a multiplicity of use parameters, usage limits, usage counts, and count limits all relating to the properties of the medical treatment system. The use parameters may include an elapsed time, a total treatment time, and a number of treatment sites. A main processor is also included for calculating a temperature from the temperature signal and for updating the use parameters in response to data received by the main processor. The main processor is also used to compare the use parameters to their corresponding usage limits. The main processor can create and increment a usage count when at least one of the use parameters exceeds its corresponding usage limit. Thereafter, the main processor compares the usage count to the count limit and disables the energy delivery device when the usage count exceeds a predetermined count limit.

20 Claims, 8 Drawing Sheets

U.S. PATENT DOCUMENTS

| | | |
|---|---|---|
| 5,651,780 A | 7/1997 | Jackson et al. |
| 5,749,871 A | 5/1998 | Hood et al. |
| 5,754,717 A | 5/1998 | Esch |
| 5,802,229 A | 9/1998 | Evans et al. |
| 5,848,209 A | 12/1998 | Evans et al. |
| 5,875,275 A | 2/1999 | Evans et al. |
| 5,946,441 A | 8/1999 | Esch |
| 5,978,541 A | 11/1999 | Doiron et al. |
| 5,991,355 A | 11/1999 | Dahlke |
| RE36,473 E | 12/1999 | Esch et al. |
| 6,237,604 B1 | 5/2001 | Burnside et al. |
| 6,361,530 B1 | 3/2002 | Mersch |
| 6,387,092 B1 | 5/2002 | Burnside et al. |
| 6,464,689 B1 | 10/2002 | Qin et al. |
| 6,611,793 B1 | 8/2003 | Burnside et al. |
| 2002/0120262 A1 | 8/2002 | Bek et al. |
| 2002/0198519 A1 | 12/2002 | Qin et al. |
| 2003/0118302 A1 | 6/2003 | James, IV et al. |
| 2004/0092919 A1 | 5/2004 | Ritchie et al. |
| 2004/0122419 A1* | 6/2004 | Neuberger .................. 606/10 |

FOREIGN PATENT DOCUMENTS

| | | |
|---|---|---|
| EP | 1201196 A | 5/2002 |
| WO | WO 92/17243 A2 | 10/1992 |
| WO | WO 99/67156 A | 12/1999 |
| WO | WO 02/35264 A1 | 5/2002 |

OTHER PUBLICATIONS

EPO Search Report dated Feb. 25, 2005 for corresponding patent application, European Patent Application No. EP 04 25 7326.

* cited by examiner

MEDICAL TREATMENT SYSTEM WITH ENERGY DELIVERY DEVICE FOR LIMITING REUSE

FIELD OF THE INVENTION

The present invention relates generally to a system for applying energy to human tissue, and more particularly, to such a system having information storage capability. The present invention also relates to a medical treatment system with an energy delivery device, and methods for use thereof, having capabilities to determine usage and to limit the number of uses or to prevent reuse of the energy delivery device after a certain threshold has been reached.

BACKGROUND OF THE INVENTION

Currently surgeons employ medical instruments that deliver energy in the treatment of benign prostatic hyperplasia, which is commonly referred to as BPH. BPH is a condition of an enlarged prostate gland, in which the gland having BPH typically increases beyond its normal size. Methods generally known as Interstitial Thermotherapy (ITT), and specifically Laser Interstitial Thermotherapy, sometimes referred to as LITT, have been widely used in the treatment of this condition. ITT utilizes energy delivery devices, often in the form of LITT using laser light sources, to treat the BPH condition using optical fibers that emit light radially in a predictable and controlled manner. The goal of LITT is to diffuse light into the human tissue in a controlled manner in order to coagulate or ablate the tissue, thus decreasing the volume of the gland and alleviating the symptoms of BPH. Similar devices are also used for Photo-Dynamic Therapy (PDT), wherein a light-activated pharmaceutical agent is used in combination with diffusing fibers to treat human diseases.

During the treatment of human tissue by LITT, accurately controlling the amount of energy diffused through the optical fiber and absorbed by the human tissue is critical to assure efficacious treatment. The amount of energy absorbed by the human tissue can be monitored by measuring the temperature at the treatment site. Even minor variations in temperature at the location being treated can change the therapeutic benefits of treatment. One difficulty with the use of fiberoptic technology to deliver energy is that the performance of the materials used to construct the fiberoptic may change with use or age. These performance changes can result in variations in the amount of energy transmission through the optical fiber, which may lead to over or undertreatment of the tissue. However, accurate measurement of the tissue temperature at the treatment site can be used to detect performance changes of the optical fiber. In particular, any inconsistencies or shifts in the tissue temperature may indicate unwanted variations in energy delivery that may lead to over treatment or under treatment of the tissue, which can result in an inferior clinical outcome.

Additionally, some fiber optic devices may be damaged or degraded as a result of the mechanical or thermal stresses incident to normal use. Excessive bending, pulling, flexing, manipulating, twisting or heating can cause changes in the performance of the fiberoptic. Even ordinary and expected usage can affect the energy delivered through the fiber optic device over an extended period of time. Use of a fiber optic device or in excess of its design expectancy or useful life can also result in further degradation of the optical fiber.

It is desirable to limit the use of the fiberoptic device based upon the extent of use or overall age of the device. By restricting the use of the device to within expected design limits, performance changes of the fiberoptic may be avoided, and the risk of a malfunction may be decreased.

Consequently, there is a need for specific medical treatment systems that prevent reuse upon detecting degradation of the optical fiber or when the expected life limits of the optical fiber have been exceeded. There is also a need for such devices that provide for monitoring of temperatures at the treatment site while also providing for limitations on reuse or overuse by giving full consideration to the multiplicity of diverse factors that can detect performance changes of the fiber optic device. Such an apparatus and methodology will help assure that fiber optic devices are not utilized in excess of their designed or useful life, and this will also help practitioners to assure that patients receive the most efficacious treatment that these devices can provide.

SUMMARY OF THE INVENTION

According to the present invention, an energy delivery device for use with a medical treatment system is provided for the efficacious treatment of patients during laser surgery. More particularly, the invention relates to an energy delivery device, wherein the energy delivery device is connected to an energy source via a connector at the proximal end and the distal end is positionable at a treatment site. The energy delivery device comprises an optical fiber and a memory device, both of which can be operatively connected to the energy delivery device during use of the medical treatment system. The memory device is preferably an electronic erasable programmable read-only memory (EEPROM) chip attached to a printed circuit board. The memory device has data programmed therein and preferably the data stored therein relates to the physical, mechanical and chemical properties of the optical fiber or the medical treatment system itself.

In one embodiment of the present invention, the energy delivery device comprises an optical fiber including a temperature sensor at a distal end thereof for generating a temperature signal in a closed loop manner. The optical fiber has multiple use parameters, a count limit, and at least one usage limit corresponding to at least one of the use parameters. The use parameters, count limit, and usage limit all relate to the properties of the medical treatment system and more particularly to the optical fiber. The use parameters, at least one usage limit, and the count limit are each stored in a memory device. The use parameters may include manufacture date and maximum allowable shelf life, elapsed time from the initiation of treatment, total power emitted, a total treatment time, and a number of treatment sites. The manufacture date indicates the date of optical fiber origination and the allowable shelf life indicates the maximum elapsed time from the date of manufacture from which the optical fiber or energy delivery device is permitted to be utilized. The last allowable date of use is preferably computed by adding the allowable shelf life to the manufacture date. The elapsed time is preferably computed by subtracting the current or present time from a baseline date and time. The baseline date and time are stored in the memory device upon initial activation of the energy delivery device. The total power emitted is preferably a cumulative measurement of the amount of power actually delivered through the device during the active treatment. The total treatment time is a cumulative measurement of the duration of time that the energy delivery device is actually activated. At least one usage limit is an elapsed time limit. The elapsed time limit can be between about one hour and about twelve hours, and in one embodiment is about one hour. Another usage limit is the last allowable date of use. The last allowable date of use is preferably about 5 years after the date of manufacture. At least one usage limit can also be a treatment time limit. The treatment time limit is preferably about 36 minutes. At least one usage limit even further can be a treatment site limit. The treatment site limit is preferably about 12 sites.

The optical fiber and the memory device are capable of being operatively connected to each other for use of the energy delivery device in accordance with this invention. A processor is also included. The processor can be used for calculating a temperature from the temperature signal that the processor receives from the temperature sensor. The processor can also be used for updating at least one of the parameters of use in response to data received by the processor. The processor can also be for comparing the use parameter to its corresponding usage limit. The processor can create and increment a usage count when at least one of the multiplicity of use parameters exceeds its corresponding usage limit. Thereafter, the processor can compare the usage count to the count limit and disable the energy delivery device without disabling the functionality of the memory device when the usage count exceeds the allowable count limit.

Numerous alternative embodiments of the present invention are disclosed herein. For example, in one alternative embodiment the optical fiber can have multiple parameters of use corresponding to at least one usage limit and the optical fiber can also have at least one count limit. A memory device can be connected to the optical fiber during manufacture of the device, prior to operative connection to energy delivery device. The multiplicity of use parameters and the usage limit and the count limit are all stored in the memory device. The processor can be used for calculating a temperature from a temperature signal received from the distal end of the optical fiber and for updating at least one of the multiplicity of use parameters in response to data received by the processor upon activation of the energy delivery device. The processor also compares the use parameter to its corresponding usage limit. One such use parameter can be the temperature or even the temperature signal itself. Additionally, one usage limit can be a maximum temperature limit or a maximum variation in the temperature signal over a period of time. Moreover, the processor can create and increment a usage count when at least one of the multiplicity of use parameters exceeds its usage limit. The processor then compares the usage count to the count limit and disables the energy delivery device when the usage count exceeds the count limit.

In another alternative embodiment, the energy delivery device can include an optical fiber that has a primary count limit and a secondary count limit. The primary count limit and said the secondary count limit are stored in the memory device. In this embodiment, the processor compares the usage count to the primary count limit and issues a warning signal or error message when the usage count exceeds the primary count limit. Additionally, the processor can compare the usage count to the secondary count limit and disable the energy delivery device or cease the supply of energy to the energy delivery device when the usage count exceeds the secondary count limit.

In yet another alternative embodiment, the processor can create and calculate a usage count from the multiplicity of use parameters. The processor can compare the multiplicity of use parameters to their corresponding usage limit. The multiplicity of use parameters can comprise an elapsed time, a total treatment time, a number of treatment sites, or any number these or other use parameters or any combination thereof. A warning can be issued by the processor when at least one of the multiplicity of use parameters exceeds its corresponding usage limit. Also the processor can compare the usage count to the count limit in order to disable the energy delivery device when the usage count exceeds the count limit. A count limit can even be predetermined and preferably such a count limit is a value from between about 1 to about 5.

In still another alternative embodiment, a method for producing a medical treatment system for the treatment of human tissue wherein the energy delivery device includes a memory device and a temperature sensor is provided. This method comprises several steps. The initial data is stored into the memory device. This data typically includes maximum limits and use parameters. The energy delivery device and the memory device are operatively connected to the energy generator. Thereafter, data is read from the memory device or data is written to the memory device. A power level is set on the energy generator for delivery through the energy delivery device. Typically, it is at this point that treatment is initiated. To keep track of the total energy delivered to the human tissue, the total energy delivered is incremented in the memory device. The temperature is controlled in a closed loop manner, which means that the temperature is read and a temperature signal is feedback to the processor, which automatically adjusts the power to control the energy output by the energy generator in order to maintain a desired temperature at the treatment site. The processor determines the maximum temperature that has been attained during the treatment. The processor also tracks the duration of time by incrementing the duration of the energy delivery. Then a determination is made as to whether the treatment at that particular site is completed. If the treatment site is not complete, then the process loops back to increment the total energy delivery and the process continues from that step. If the treatment at that particular site is complete then the treatment site data is incremented by the processor. The usage-related parameters are then updated in the memory device. Next a determination is made as to whether the entire treatment or procedure is completed. If the procedure is not finished, the initiation of treatment continues at another treatment site. If the treatment is complete, then the treatment is ceased and the power to the energy delivery device is turned off.

While the above-identified steps are occuring, a particularly preferred method of using the medical treatment system also provides for steps to be performed simultaneously or in parallel. In particular, after data has been stored or written to the memory device or read therefrom, that data can be compared to its corresponding maximum limits. A determination regarding whether the particular use parameter exceeds its limit can be made. If the limit has not been exceeded, then the energy delivery device is allowed to function in its normal manner. A portion of that normal mode of operation is to continuously monitor the use parameters and update the data in the memory device. If the use parameter has been exceeded, then the optical fiber is no longer useable. Since the energy delivery device is no longer useable, its use is disabled. A warning can be displayed or enunciated to notify the user of this condition. Also, this end of life condition is stored in the memory device so that although the energy delivery device will be permanently disabled to avoid future reuse of the energy delivery device, a user will still be able to access the data relating to this condition from the memory device. Moreover, additional steps can be provided without detracting from the primary purpose of the invention at hand.

A further particularly preferred method of using the medical treatment system is to read and interpret the medical treatment system or medical procedure data stored in the memory device after the medical procedure is completed. This step could be performed at the site of treatment, and used to obtain a record of the treatment by the medical personnel, or could be performed during subsequent analysis of energy delivery devices which are have been reported to be defective to obtain information on energy delivery device usage and history.

The present invention thus provides an energy delivery device for applying energy to human tissue with or without a closed loop type of temperature measurement, which includes an optical fiber and a memory device wherein the memory device has data programmed therein that is specifically associated with the operational characteristics of the optical fiber and wherein the energy delivery device can be disabled when it reaches the end of its effective life. The present invention also provides methods of use associated therewith, as further described herein.

Additional advantages and features of the present invention will become more apparent from the following detailed description which may be best understood with reference to and in conjunction with the accompanying drawings.

DETAILED DESCRIPTION OF THE INVENTION

Figure 1:
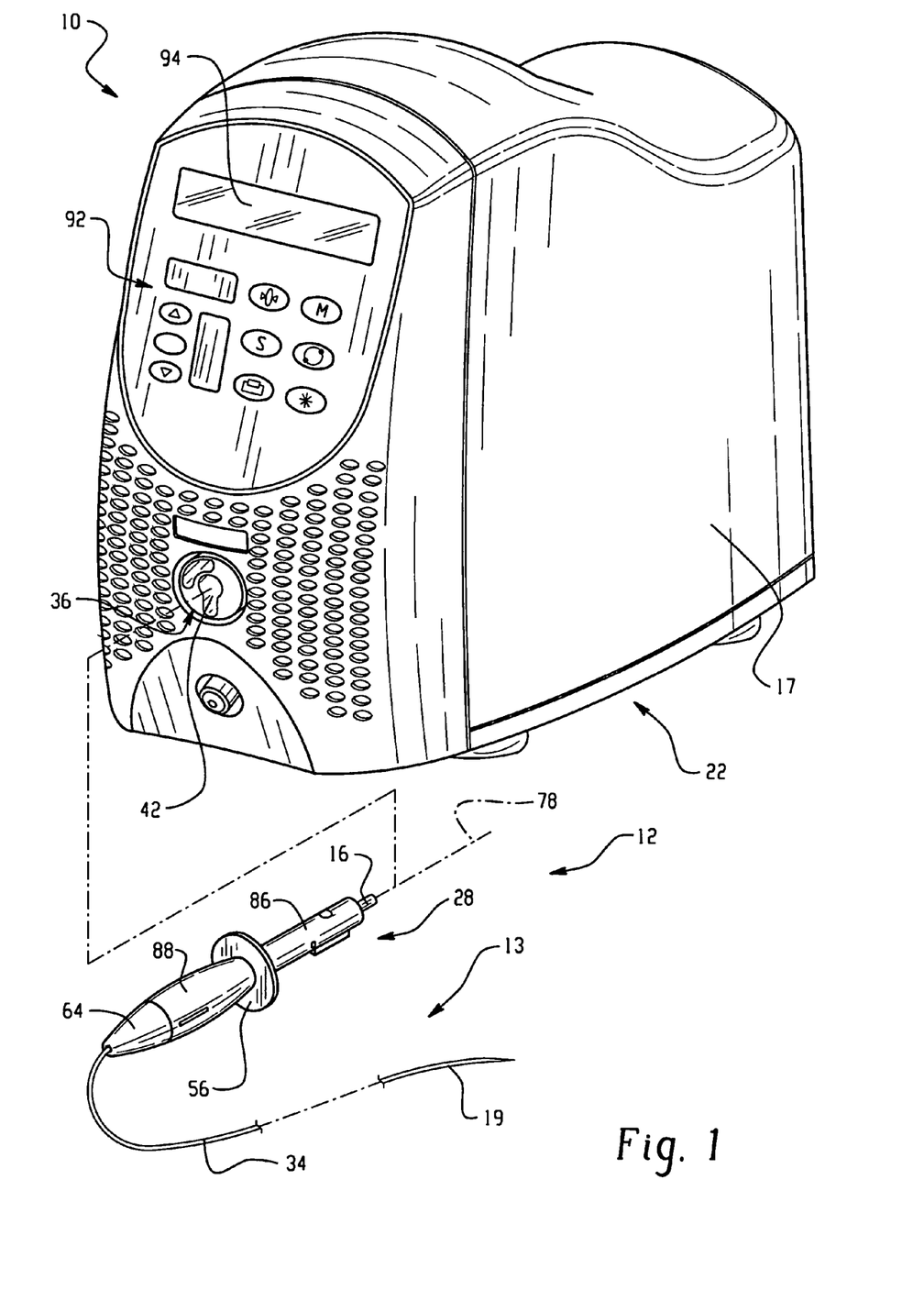
FIG. 1 is an isometric view of a medical treatment system, including an energy generator and an energy delivery device according to an embodiment of the present invention.

In this description of preferred embodiments, "means for generating energy" and "energy generator," "energy source," "generator" or "generating means" or the like, can be used interchangeably and, similarly, "delivering means" and "energy delivery device," "delivery device" or the like, can be used interchangeably unless otherwise specified. Additional terms may be used in the same manner, as will be clear to the reader. Further, the terms "proximal" and "distal" are used to refer to relative locations nearest to and farthest from, respectively, the ferrule 16 in connector 28 of the energy delivery device 12 of the medical treatment system 10, as shown in FIG. 1. These conventions are adopted merely by way of convenience, not by way of limitation.

According to an embodiment of the present invention shown in FIG. 1, medical treatment system 10 for transferring diffused light energy to human tissue (not shown) which includes energy generator 22 and energy delivery device 12, is illustrated in a disconnected configuration. In the preferred embodiment of an energy generator 22 shown, energy is generated in the form of laser light. Nonetheless, energy generator 22 could be any means for generating energy or a generator for many deferent types of energy such as, for example, laser light energy, infrared energy, radio frequency energy, microwave energy, ultrasound energy or any other energy suitable for the treatment of human tissue. By way of example, a means for generating ultrasonic energy may be the Ultracision Harmonic Scalpel commercially available from Ethicon Endo-Surgery Inc., of Cincinnati, Ohio, and a means for generating radio-frequency energy may be any of a variety of surgical generators, such as the ICC 350 Electrosurgical Generator commercially available from Erbe USA, Inc., of Marietta, Ga. Preferably, energy generator 22 is a portable diode based laser, and most preferably, the Indigo® Optima laser system commercially available from Ethicon Endo-Surgery, Inc. of Cincinnati, Ohio.

A cover 17 shields interior components of energy generator 22, and a connector housing 36 resides within a front portion of cover 17. The front of connector housing 36 is exposed to the exterior. Medical treatment system 10 further includes an energy delivery device 12 having connector 28 at its proximal end and optical fiber 13 at its distal end. The optical fiber 13 of energy delivery device 12 extends from connector 28 to light-emitting section 19. Optical fiber 13 could be associated with any energy delivery device 12 capable of delivering useful energy such as, for example, laser light energy, infrared energy, radio frequency energy, microwave energy, ultrasound energy or any other energy suitable for the treatment of human tissue. Energy delivery device 12 could be any means for delivering energy or any device capable of delivering many types of useful energy from the energy generator 22.

Energy delivery device 12 is attachable to connector housing 36 by inserting connector 28 through an opening 42 in connector housing 36 to lock the connector 28 in position. Connector 28 inserts into connector housing 36 and locks into connector housing 36 by rotation about a longitudinal axis 78. In one embodiment, energy delivery device 12 may be a disposable delivery device with a limited useful life, including data stored therein in the form of use parameters which assist in defining reuse limitations, for delivering energy from an energy generator 22 to human tissue. In this embodiment, energy delivery device 12 can be removed from energy generator 22 by unlocking connector 28 from connector housing 36 by rotation about a longitudinal axis 78 in a direction opposite the locking rotation.

As shown in FIG. 1, the energy generator 22 may include a keypad 92 on cover 17 for user interface and input of data. The energy generator 22 may also include a display screen 94 on cover 17 for the display of data, warnings, or other information.

Figure 2:
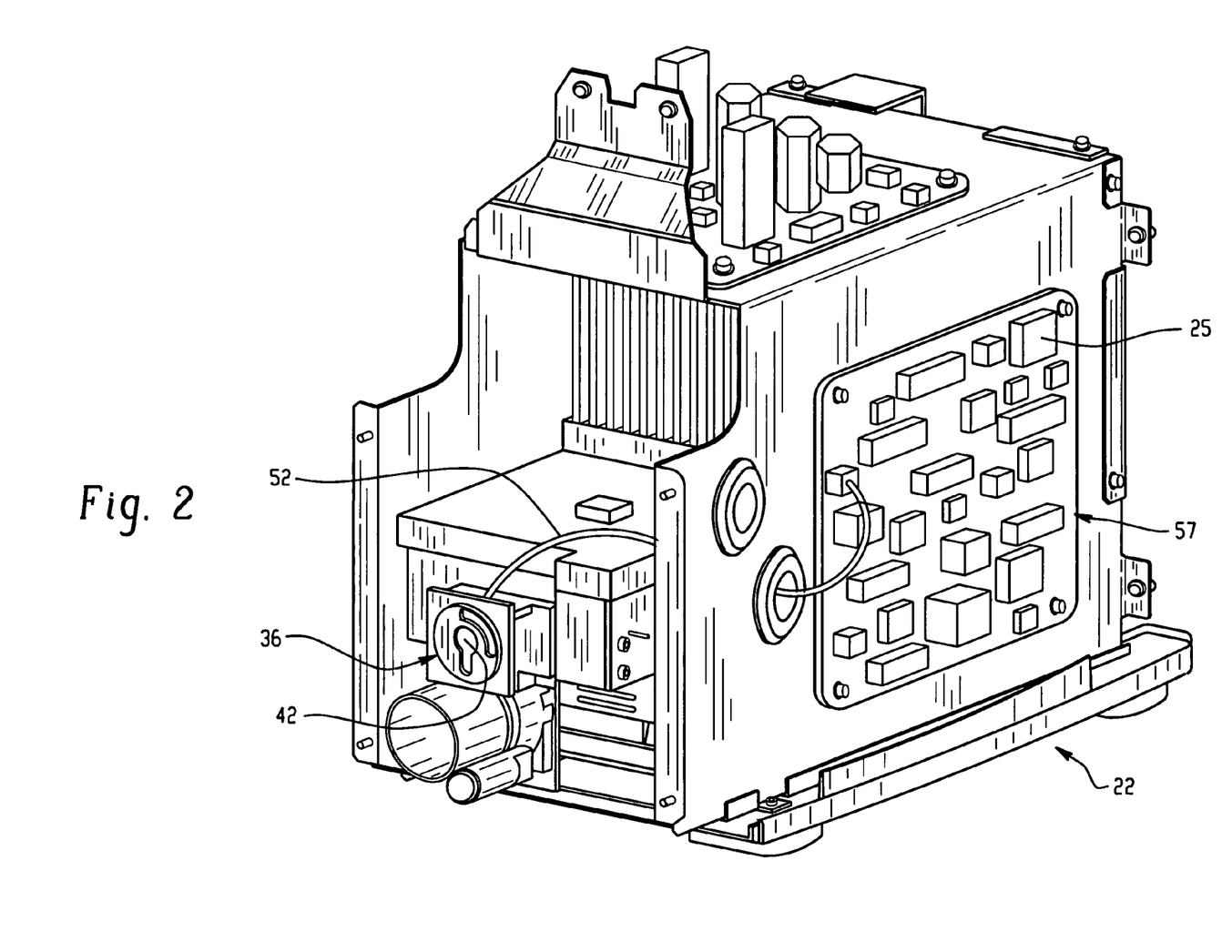
FIG. 2 is an isometric view of the energy generator of FIG. 1 with the cover removed for clarity.

FIG. 2 depicts energy generator 22 with cover 17 removed to expose interior portions of energy generator 22. Conductor cable 52 electrically joins connector housing 36 to controller board 57 on energy generator 22. Located on controller board 57 is a computer in the form of main processor 25, which receives and processes electronic signals to control the operation of medical treatment system 10. Main processor 25 can be, for example, a microprocessor or miniature computer. Signals from electronic components within energy delivery device 12 communicate via conductor cable 52 with controller board 57 and main processor 25. Additionally, the main processor 25 can be operatively connected to the keypad 92 and the display screen 94.

In operation, the main processor 25 directs the energy application process according to instructions from the user via the keypad 92 or programmed instructions from the energy delivery device 12, as further described herein. The main processor 25 communicates information concerning the process to the display screen 94 for observation by the user. Main processor 25 may also enunciate information in an audible manner using methods known in the art. Should the user find the information concerning the process undesirable, for example, unsafe to the patient undergoing treatment, he or she may override the operating instructions via the keypad 92.

Figure 3:
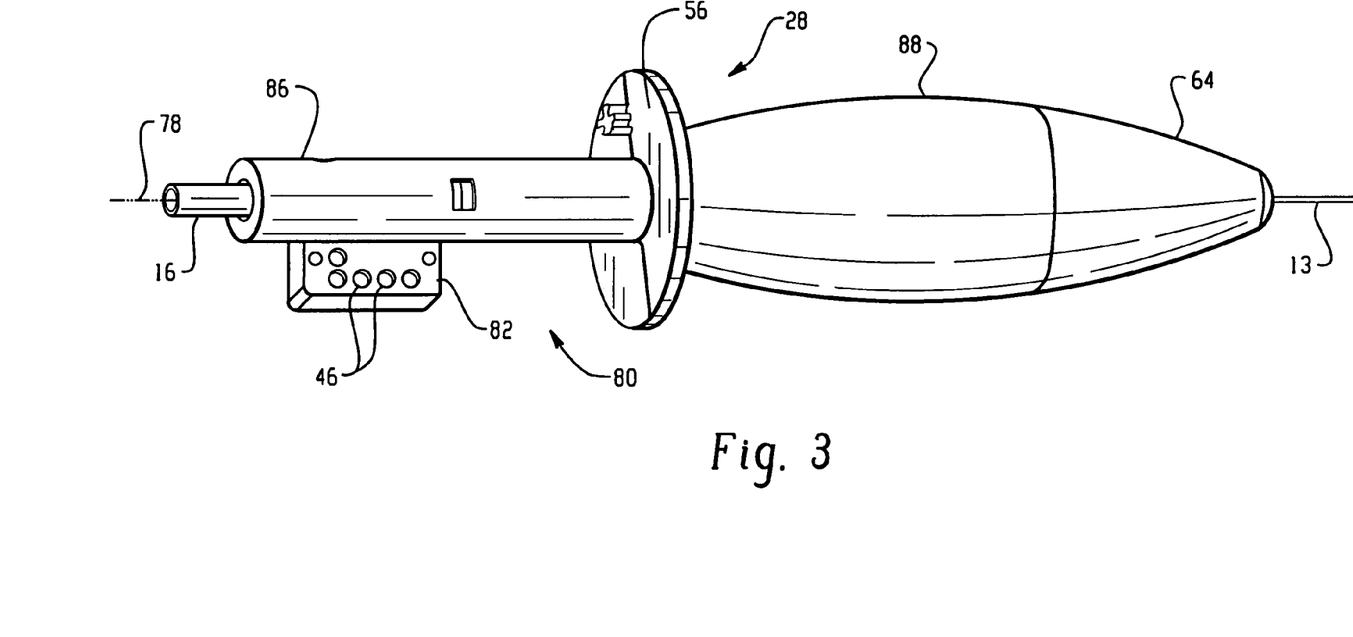
FIG. 3 is an isometric view of the connector of FIG. 1.

As shown in FIG. 3, connector 28 possesses a handle portion 88, shaped for easy grasping by the user, and capped on the distal end with a boot 64. Optical fiber 13 extends distally from the boot 64. A barrel 86 continues proximately from handle portion 88. A connector face 56 separates barrel 86 from handle portion 88. Attached to barrel 86 is a flange 82 radially extending from longitudinal axis 78. Flange 82 includes contact pad access openings 46 placed on a large side of flange 82. An axial gap 80 separates the distal end of flange 82 from connector face 56. Ferrule 16 is located within connector 28 and a portion of ferrule 16 protrudes from the proximate end of barrel 86. Ferrule 16 is one form of an energy transfer attachment for transferring energy from energy generator 22 to energy delivery device 12 for medical treatment. Opening 42 on connector housing 36 allows entrance of barrel 86 of connector 28 to operatively connect the energy delivery device 12 to the energy generator 22.

Figure 4:
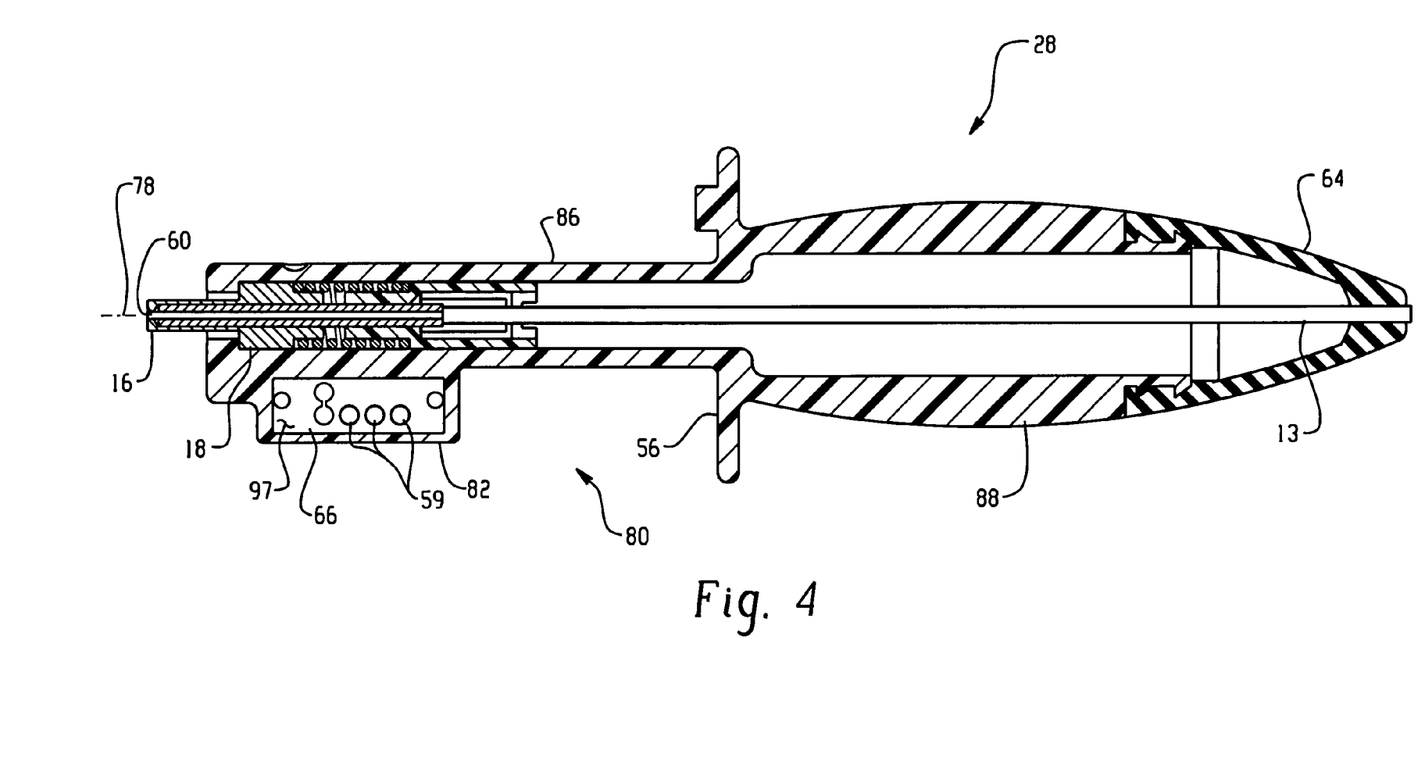
FIG. 4 is a sectional view taken in side elevation along the centerline of the connector shown in FIG. 3.

A cross sectional view of connector 28 is shown in FIG. 4 depicting the interior portions of connector 28. Ferrule 16 has a passageway 60 through the center thereof to admit light energy generated by energy generator 22 into optical fiber 13. The passageway 60 in ferrule 16 is coaxial with longitudinal axis 78. The interior of handle portion 88 engages enlarged portion 18 of ferrule 16 and boot 64 surrounds and retains optical fiber 13 as it emerges from handle portion 88 of connector 28. Printed circuit board 66 within flange 82 is also illustrated with mating surface 97. Printed circuit board 66 can be inset-molded into flange 82 leaving only contact pads 59 open to the exterior through access openings 46. Connector 28 is preferably molded of non-conductive material such as plastic.

Figure 5:
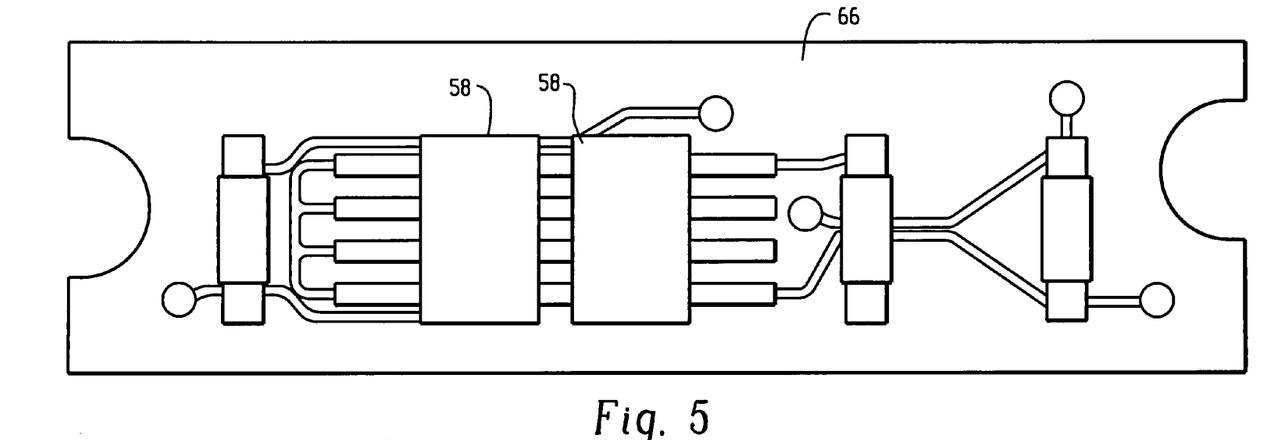
FIG. 5 is a plan view showing an opposite side of the printed circuit board of FIG. 4.

FIG. 5 depicts the side of printed circuit board 66 opposite that shown in FIG. 4. A memory device 58 resides on the side of printed circuit board 66 opposite mating surface 97 and is in electrical communication with contact pads 59. Memory device 58 can be, for example, an electronic erasable programmable read-only memory device (EEPROM) and can store information useful to the operation of energy delivery device 12 and medical treatment system 10.

With connector 28 in the locked position, memory device 58 can communicate electrically with main processor 25 on controller board 57 through contact pads 59 and conductor cable 52. Information within memory device 58 may now be accessed by main processor 25 and vice versa.

While the memory device 58 has been described as an EEPROM, which may store a significant amount of data, it may alternatively be any non-volatile type memory of a variety of digital, optical, or magnetic memory storage devices or integrated circuits providing memory capability. For example, such memory device 58 may include read-only memory (ROM), programmable read-only memory (PROM), erasable programmable read-only memory (EPROM), flash memory, non-volatile random access memory (RAM), or most preferably EEPROM. Of course, the entire set of data or information need not be stored in a single memory device 58 or in a single type of memory device 58, for it is understood that multiple memory devices 58 of multiple types can be used in accordance with the present invention. Further, while the memory device 58 has been described as being mounted on printed circuit board 66 which is inset molded on flange 82, it is understood that printed circuit board 66 or memory device 58 can alternatively be externally mounted or even a wholly separate assembly or device that operatively connects to energy generator 22 or energy delivery device 12 via a separate electrical connection or some other method of connection. Additionally, memory device 58 can be operatively connected to optical fiber 13 from a location remote from energy delivery device 12 without varying from the scope of this invention. Operatively connected as used herein refers to the ability of components to transmit energy or to exchange data such as via the communication of electronic data between each component. Moreover, while the exchange of data between the memory device 58 and the energy generator 22 has been described as possibly being accomplished via electrical means, it may alternatively be accomplished via magnetic, infrared, radio frequency or even optical means. These alternatives and others, which may be arrived at by one of ordinary skill in the art without undue experimentation, and are contemplated as being within the scope of the present invention.

An energy delivery device 12 used for these purposes typically extends from a connector 28 to at least the distal end of the optical fiber 13. Preferably, the energy delivery device 12 includes a means for emitting energy from the energy delivery device 12 to the human tissue at or near its distal end. In particular, medical treatment system 10, with energy delivery device 12, can be used to apply laser light energy to human tissue for therapeutic treatment of the human tissue, for example, for treatment of diseases such as BPH using LITT.

Figure 6:
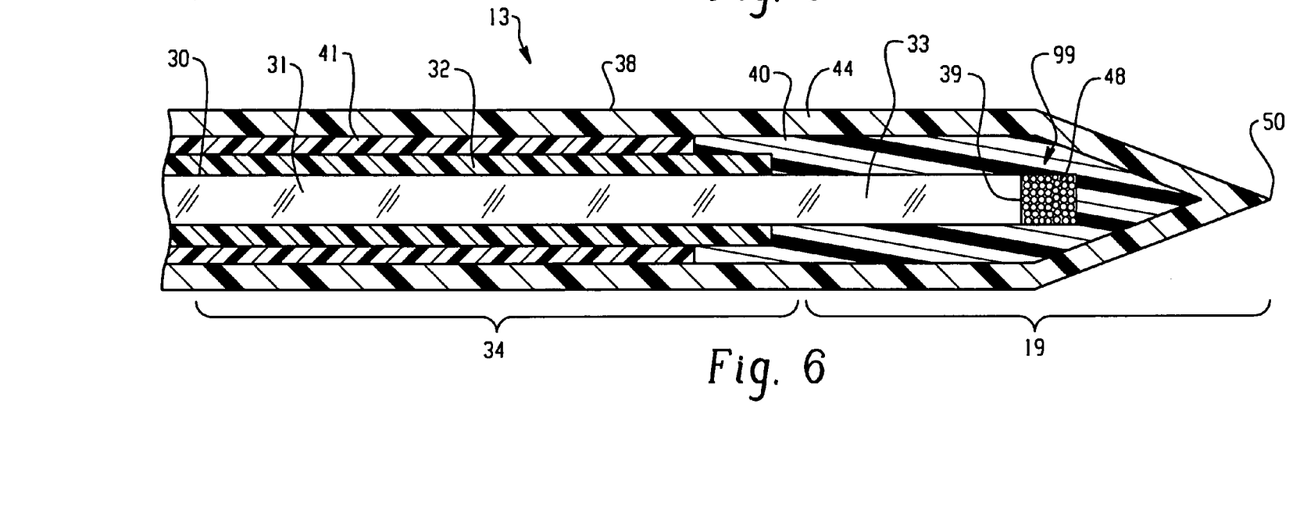
FIG. 6 is a sectional view taken in side elevation of an optical fiber of FIG. 1.

Now referring to FIG. 6, an energy delivery device 12 according to one embodiment of the present invention, includes an optical fiber 13 comprising a diffuser or light-emitting section 19 at its distal end and a non-diffusing or light-transmitting portion 34 extending toward its proximal end. In light-transmitting portion 34 of optical fiber 13, a cladding 32 and the proximal portion of a sheath or sleeve 38 radially surround the proximal portion 30 of core 31. Optical fiber 13 may have a jacket or buffer layer 41 arranged to extend circumferentially between the cladding 32 and the sleeve 38. The material used to form the cladding 32 has an index of refraction lower than the index of refraction of the material used to create the glass or core 31 so as to contain the light within the core 31 throughout the length of the light-transmitting portion 34. In light-diffusing section 19 of optical fiber 13, the core 31 extends beyond its proximal portion 30 through a distal portion 33 to the distal end 39 thereof. The distal portion 33 of the core 31, which is employed to diffuse light, is surrounded by an optical coupling layer 40 and the distal portion 44 of the sleeve 38 thereby forming the light-diffusing section 19 without the cladding 32 of the light-transmitting portion 34.

A material having an index of refraction higher than the index of refraction of the core 31 forms the optical coupling layer 40. Preferably, UV50 Adhesive, commercially available from Chemence, Incorporated, in Alpharetta, Ga., is the adhesive used to produce the optical coupling layer 40. Other adhesives which may be used include XE5844 Silicone, available from General Electric Company and 144-M available from Dymax of Torrington, Conn.

The sleeve 38 can extend distally past the distal end 39 of the core 31 and may be configured to form a sharp or pointed penetrating tip 50. Penetrating tip 50 is capable of piercing through human tissue in order to enable medical procedures. In a preferred embodiment, sleeve 38 constitutes one continuous piece, more preferably sleeve 38 consists of perfluoroalkoxy impregnated with barium sulfate.

A light-scattering component 48 which is filled with a light-scattering material and located on the distal end 39 of the core 31 can reflect light back into the core 31 so as to provide a more even or uniform light distribution. Alexandrite particles can be employed as the light-scattering material for light-scattering component 48. In addition to its light-scattering properties, the light-scattering component 48 fluoresces in a temperature-dependent manner upon being stimulated by light. For example, some of the light energy absorbed by the light-scattering component 48 causes the stimulation of the light-scattering component 48 which then generates and releases light energy back into the core 31 toward the proximal end in the form of a temperature signal having a longer wavelength and a phase or time delay. The frequency or time delay between the light energy absorbed by the light-scattering component 48 and the emission of the light energy from the light-scattering component 48 is dependent on the temperature of light-scattering component 48. Main processor 25 calculates the temperature by use of this phase difference or temperature signal, which it converts into a temperature measurement. It is this temperature-dependent fluorescence property of the light-scattering component 48 that is adapted to be used as a temperature sensor 99. Thus, the fluorescent properties of the alexandrite particles, when stimulated by light energy of the proper wavelength, can allow the determination of the temperature of surrounding human tissue by other methods which are known in the art. In this closed loop manner an indication or measurement of temperature in the human tissue at the treatment location in proximity to the light-diffusing section 19 or penetrating tip 50 is obtained.

Figure 7:
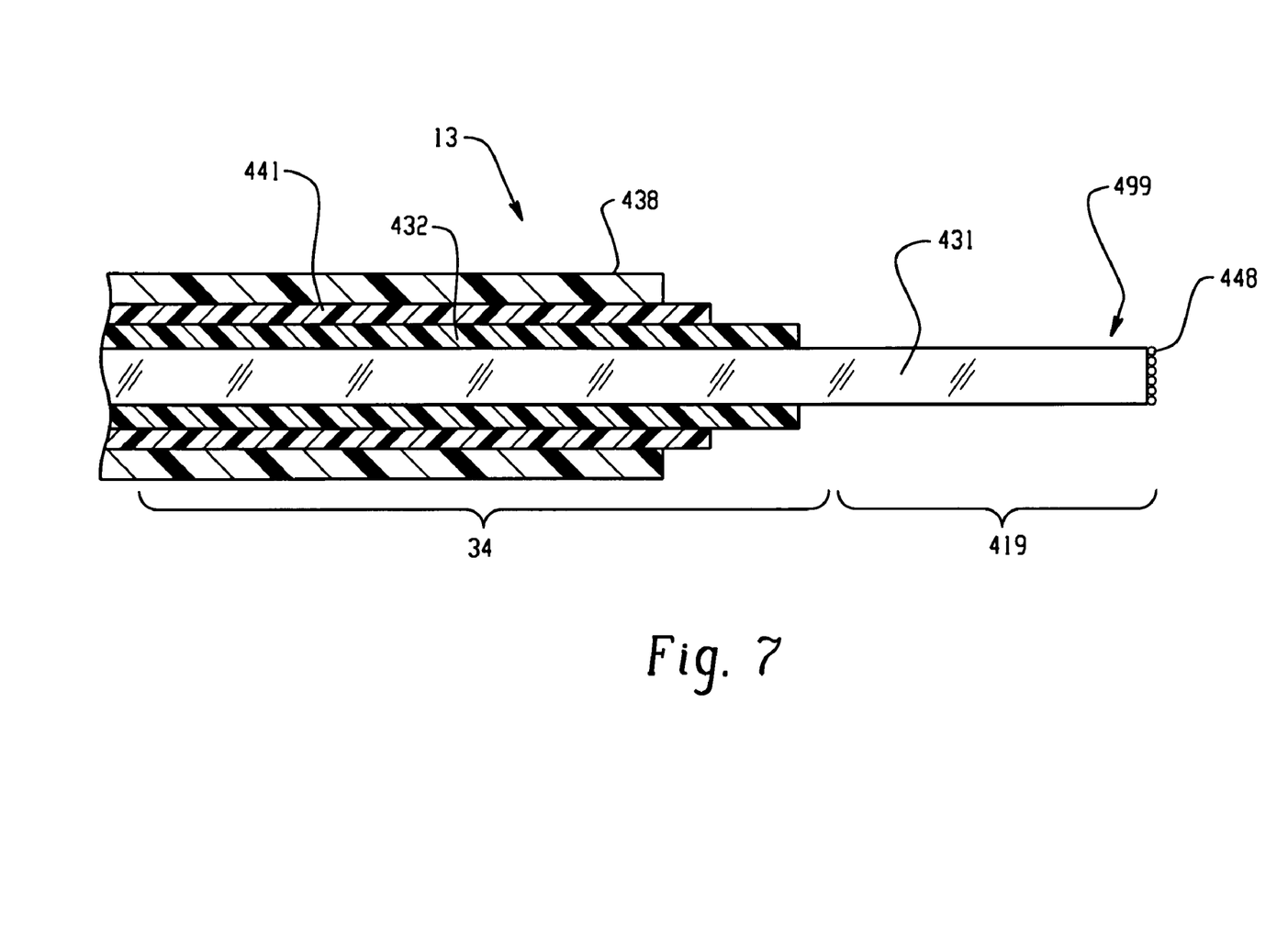
FIG. 7 is a sectional view taken in side elevation of an alternative embodiment of an optical fiber of FIG. 1.

Alternatively, the optical fiber 13 shown in FIG. 7 can be provided with a cutting or ablating section 419. In particular, core 431 is preferably formed of a silica fiber and extends distally beyond where sleeve 438, buffer layer 441 and cladding 432 ends to a tip 499 embedded with silicon carbide material 448. This exposed portion of core 431 is indicated generally as ablating section 419. In this configuration, core 431 is exposed or bare at the ablating section 419 and the light energy is emitted therefrom. Such an optical fiber 13 is typically referred to as a bare fiber. During operation, light energy generated by energy generator 22 travels through core 431 to ablating section 419 and at ablating section 419 the light energy is absorbed by core 431 at ablating section 419. This causes tip 499 of ablating section 419 to heat up. Consequently, this bare optical fiber 13 can be used to cut, ablate, or coagulate when tip 499 of ablating section 419 comes into contact with the human tissue.

Preferably, the energy delivery device 12 with connector 28 is the fiberoptic system associated with the Indigo® Optima laser system, which is also commercially available from Ethicon Endo-Surgery Inc. The energy delivery device 12 along with the energy generator 22 are further described and disclosed in U.S. Pat. No. 6,522,806, entitled "Optical Fiber Including A Diffuser Portion And Continuous Sleeve For The Transmission Of Light" issued to James, IV et al. on Feb. 18, 2003; U.S. patent application Pub. No. 2001/0025173, entitled "Energy Application System With Ancillary Information Exchange Capability, Energy Applicator, And Methods Associated Therewith" by Ritchie et al. and published on Sep. 27, 2001; U.S. patent application Pub. No. 2002/0081871, entitled "Connector Incorporating A Contact Pad Surface On A Plane Parallel To A Longitudinal Axis" by Swayze et al. and published on Jun. 27, 2002; and U.S. patent application Pub. No. 2003/0118302, entitled "Optical Fiber Including A Diffuser Portion And Continuous Sleeve For The Transmission Of Light" by James, IV et al. and published on Jun. 26, 2003, each of which, including the entire disclosures thereof, are hereby incorporated herein by this reference.

A variety of data and information can be converted into digital form and then loaded, stored or programmed into memory device 58. Methods of storing this data and information in a digital form are well known in the art. Parameters are used or established that relate to this particular data and information. The word parameter, as used herein, is used as a symbol representing variables, functions, constants, and parametric equations.

A preferred embodiment of this invention is to determine when energy delivery device 12 has been used, to track the uses either by number or otherwise, and to determine when an end of life condition has occurred based on a use or usage-related parameter. By way of example, usage-related parameters can be preset during manufacture or can be set during use and may include or be derived from data and information relating to the medical treatment system 10 that is static (having a fixed value) or that is dynamic (having a changeable or variable value) such as any of the following: identification of the delivering means; expiration, or non-expiration date of the delivering means; calibration parameters; scale and offset factors; self heating characteristics; type of energy delivery; operational parameters; energy delivery parameters; monitoring sequence parameters; identification of the generating means; amount of energy delivery; maximum power; power range; power transmittance; data integrity factors; time from the initial recognition of the energy source; identification numbers; lot numbers; expiration date; prior usage history; energy delivery time; rate of energy delivery; total joules delivered; number of treatment sites; identification, type, date, or time of treatment; total treatment time; duration of treatment; time of treatment at each site; treatment type; mode of operation; elapsed time; total elapsed time of all treatments; temperature levels at treatment sites; identification of multiple generating means; historical data regarding attainment of certain temperature levels or power levels; historical data regarding use by multiple generating means; indication or identification of error or warning; or any abnormal or premature termination of treatment including any problem conditions triggered during any treatments; and any combination or combinations thereof. Such usage-related parameters may also include various other data and information relating to the operation of optical fiber 13, energy delivery device 12, energy generator 22, or medical treatment system 10.

It is apparent that optical fiber 13 has a multiplicity of use parameters stored in its memory device 58. How this data and information is utilized will be described in more detail below.

Main processor 25 may use the data and information stored within memory device 58 to automatically modify the energy output of energy generator 22. Also, main processor 25 may make decisions regarding the information contained within memory device 58. For example, when power is applied to activate or energize energy delivery device 12, main processor 25 may increase, decrease, disable, or even shut off the energy delivered by energy generator 22 based on the particular data and information communicated between the main processor 25 and memory device 58.

As a further example, main processor 25 may generate messages including error messages regarding the data and enunciate them audibly or display them on display screen 94 of energy generator 22. For example, an error message may be displayed if the life limit of the optical fiber 13 is exceeded upon reading the data stored in memory device 58. Main processor 25 may even write information to memory device 58 to be permanently maintained in memory device 58 with energy delivery device 12. For example, main processor 25 may write to memory device 58 or read from memory device 58 any of the aforementioned usage-related parameters or any other operational characteristics of the energy delivery device 12 even after the life limit has been exceeded.

In one particularly preferred embodiment of the present invention, the energy delivery device 12 includes optical fiber 13 with a temperature sensor 99 at a distal end for generating a temperature signal in the previously identified closed loop manner. In this embodiment, optical fiber 13 has a multiplicity of use parameters and a count limit and at least one usage limit corresponding to at least one of the multiplicity of use parameters. The use parameters and count limit and usage limit all relate to the operational characteristics or fundamental properties of optical fiber 13 or medical treatment system 10. These use parameters and usage limit and count limit are all stored in memory device 58. The use parameters may include a variety of dynamic data and information which can be identified during the medical procedure such as the elapsed time of the procedure, the total treatment time, or the number of human tissue treatment sites. The elapsed time is preferably computed based on the identifying the time that the treatment was initiated. The exact date and time that the treatment was first initiated or alternatively the exact date and time that the energy delivery device 12 was first initially activated is referred to herein as the baseline date and time respectively. The elapsed time is computed by subtracting the current or present time from the baseline date and time. The baseline date and time are stored in memory device 58. At least one of the usage limits can be an elapsed time limit. Preferably, the elapsed time limit is a total of about 12 hours. The total treatment time is a cumulative measurement of the duration of time that the energy delivery device 12 is actually energized or actually activated. At least one of the usage limits can also be a treatment time limit. The treatment time limit is preferably a total time of about 36 minutes. During the medical procedure, a number of different locations of the human tissue may need to be treated. Each of these locations is known as a treatment site. At least one of the usage limits can also be a treatment site limit. A preferable treatment site limit is about 12 sites. The values determined for these limits have been predetermined in order to avoid degradation or failure of the particular type of optical fiber 13 being used. Consequently, while these limits may be referred to as the useful life expectancy or life limits relating to energy delivery device 12 and optical fiber 13, they are not intended to indicate that the efficacy of energy delivery device 12 has in any manner become diminished or that energy delivery device 12 will fail or that the energy delivery device 12 can not, in all instances, be used for some duration or term in excess of such limits.

Main processor 25 is used to calculate the actual temperature at the treatment site from the temperature signal that main processor 25 receives from the temperature sensor 99. Main processor 25 can also be used for updating at least one of the use parameters in response to data received by main processor 25. Main processor 25 is also used for comparing one or more of the use parameters to its corresponding usage limit. Main processor 25 can create and increment a usage count when at least one of the of use parameters exceeds its corresponding usage limit. Typically, main processor 25 is programmed to increment the usage count by an incremental value of one when the use parameter is greater than its corresponding usage limit. However, main processor 25 may be programmed to utilize some other predetermined incremental value, algorithm, or formula when the use parameter exceeds its limit or to determine whether the use parameter has exceeded its limit. When the energy delivery device 12 is initially utilized there may not be any value in memory device 58 corresponding to a usage count. In this instance, main processor 25 will create a usage count and before it is incremented, the usage count may be null or zero. Thereafter, main processor 25 can compare the usage count to the count limit and disable the energy delivery device 12 when the usage count exceeds an allowable count limit. Preferably the count limit can be a value between about 1 to about 5.

For example, the use limits may be set as follows: elapsed time limit=12 hours; treatment time limit=36 minutes; treatment site limit=12 sites; count limit=1; and the usage count is set to be incremented by one. In this instance, when any one of the usage-related parameters (elapsed time, treatment time or treatment sites) exceeds its use limit, the new usage count becomes usage count+1. Thereafter the new usage count is compared to the count limit. When the new usage count exceeds the count limit of 1, main processor 25 will disable energy delivery device 12.

Numerous alternative embodiments of the present invention will now be described. For example, in one alternative embodiment, optical fiber 13 can have a multiplicity of use parameters corresponding to a single usage limit and optical fiber 13 can also have multiple count limits. The multiplicity of use parameters and the usage limit and the count limit can all be stored in a separate memory device 58 or in one common memory device 58.

One alternative use parameter can be the temperature measured at the treatment site or even the temperature signal itself. One usage limit can be a maximum temperature limit. In particular, if the temperature were to exceed a set maximum temperature, this could indicate that the human tissue at the treatment site is being over heated or that optical fiber 13 has degraded to an extent that an erroneous temperature is being detected. Either condition should be avoided and thus, exceeding a maximum temperature limit could cause main processor 25 to disable energy delivery device 12. Additionally, an unexpected variation in the frequency of the temperature signal over a period of time can be an indicator that optical fiber 13 or energy delivery device 12 has become degraded. In this instance, the use parameter can be the temperature signal or the frequency of the temperature signal. A maximum or minimum value of such temperature signal can be set as a usage limit. Moreover, main processor 25 can be programmed to create and increment a usage count when multiple use parameters exceed their usage limits.

In another alternative embodiment, the energy delivery device 12 can include an optical fiber 13 that has a corresponding primary count limit and a secondary count limit. The primary count limit and said the secondary count limit are stored in memory device 58. In this embodiment, main processor 25 can compare the usage count to the primary count limit and display, enunciate or issue a warning signal or some other type of error message when the usage count exceeds the primary count limit. Thereafter, main processor 25 would compare the usage count to the secondary count limit and disable the energy delivery device 12 or cease the supply of energy to the energy delivery device 12 when the usage count exceeds the secondary count limit.

In yet another alternative embodiment, main processor 25 can create and calculate a usage count from the multiplicity of use parameters based on a preset formula or algorithm. The multiplicity of use parameters could be an elapsed time, total treatment time, number of treatment sites, or any number of these or other use parameters or any combination thereof. Main processor 25 could then compare the usage count to the corresponding usage limit. For example, the use parameters are as follows: initial usage count=0; elapsed time=ET; treatment time=TT; treatment site=TS; count limit=5; and (ET/6)+(TT/12)+(TS/12)=usage count. In this instance, the usage count must be calculated and then compared to the count limit. When elapsed time=12 hours, treatment time=36 minutes, and treatment sites=12 sites, the calculated usage count equals 6. Since this usage count exceeds the count limit of 5, main processor 25 will disable energy delivery device 12. In this same manner, the usage parameters can be tailored for use with a wide variety of types and configurations of optical fibers 13 in order to determine when their effective life limits have been achieved.

In another alternative embodiment, the energy delivery device 12 can include an optical fiber 13 that has a date of manufacture and a maximum allowable shelf life. The manufacture date and maximum allowable shelf life are stored in memory device 58. In this embodiment, main processor 25 can compare the current date to the sum of the manufacture date and maximum allowable shelf life, and enunciate or issue a warning signal or some other type of error message when the actual use date exceeds the allowable shelf life, thus preventing use of the energy delivery device beyond a given time frame. In this instance, the maximum allowable shelf life is when the optical fiber was manufactured more than about 12 months, or more preferably about 60 months, prior to the actual use date and at that point in time, main processor 25 will disable energy delivery device 12. In other words the shelf life has expired when the current date exceeds or is greater than the manufacture date plus about 12 months to about 60 months. In this same manner, the use parameters can be tailored for use with a wide variety of types and configurations of optical fibers 13 in order to determine when their effective usage limits have been achieved.

Upon connection of the energy delivery device 12 to the energy generator 22, the energy delivery device 12 is ready to receive energy from the energy generator 22 and deliver the energy to the human tissue from its light-emitting section 19 of optical fiber 13. The medical treatment system 10 including energy generator 22 is made ready to limit the reuse of energy delivery device 12 in the treatment of human tissue when memory device 58 is operatively connected with optical fiber 13 as previously described.

Figure 8:
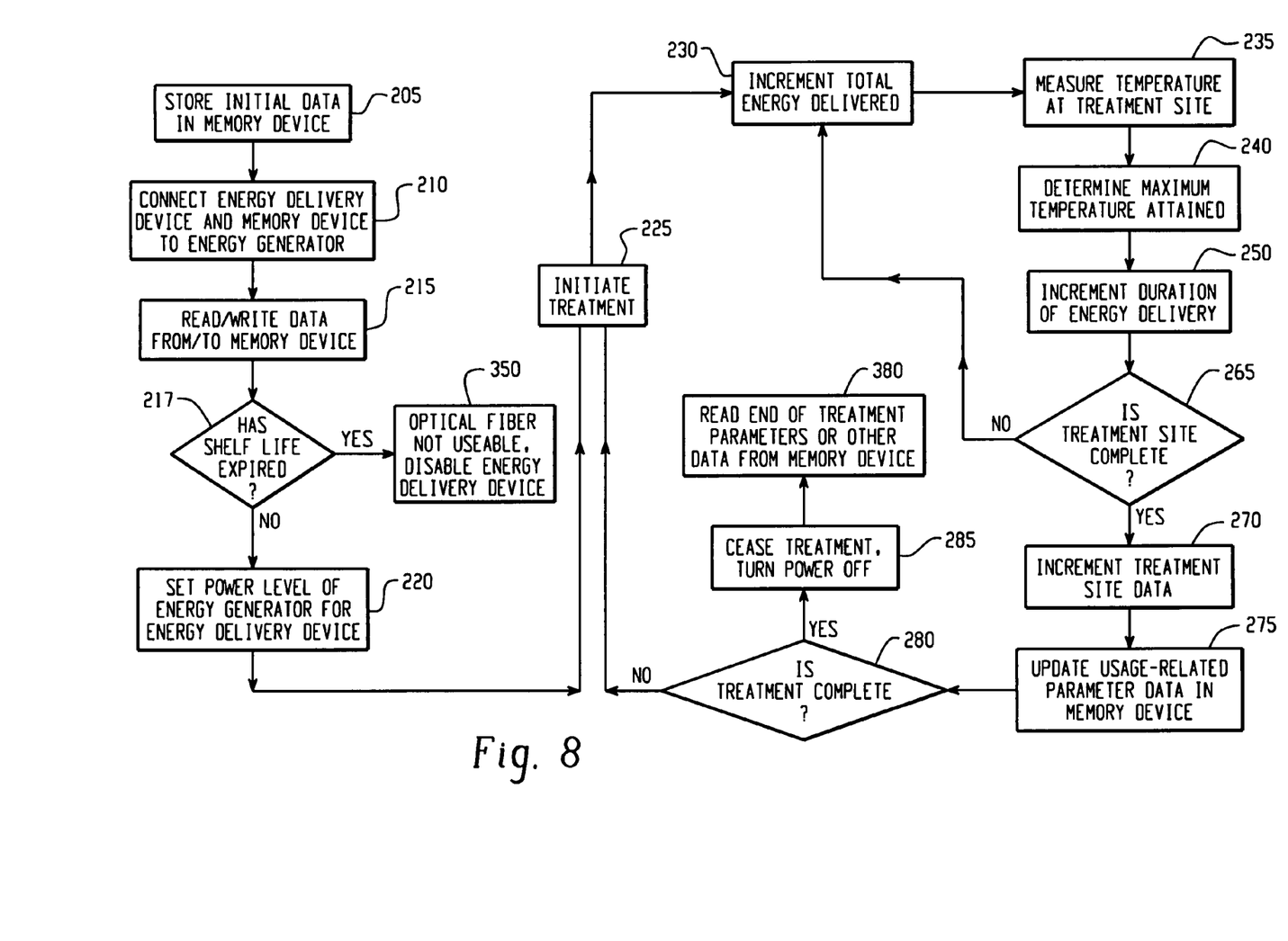
FIG. 8 is a flow chart illustrating a method for use of an energy delivery device in accordance with the present invention.

Now referring to the method of limiting use of the medical treatment system 10 shown in FIG. 8, it will be apparent to those of ordinary skill in the art that the previously identified data and information can be stored in memory device 58 in a variety of ways known to those of ordinary skill in the art [205]. In this embodiment of the invention, the preferred manner of operatively connecting energy delivery device 12 and memory device 58 to energy generator 22 is by a direct electrical connection [210]. Upon engaging the memory device 58, main processor 25 of energy generator 22 can read the various pieces of data and information from or write the data and information to memory device 58, including operational characteristics, limits, calibration parameters, coefficients, usage-related parameters and other data as described previously [215]. The processor now can determine whether the shelf life has expired [217]. In particular, if the current date exceeds the manufacture date by more than 12 months, or more preferably by 60 months, then the shelf life has expired. If the shelf life has expired, the optical fiber 13 is no longer useable and the energy delivery device 12 is disabled [350].

In the event that the shelf life has not expired, a user of the medical treatment system 10 then sets an initial power level of energy generator 22 for the specific therapeutic use of energy delivery device 12 [220]. Various power levels may be desired based on the type of human tissue, type of treatment, and location to be treated. The user typically initiates the treatment by penetrating the human tissue using penetrating tip 50 and positioning light-diffusing section 19 of energy delivery device 12 in close proximity to the region of human tissue to be treated [225]. Power is then applied to activate energy delivery device 12. The baseline date and time is then stored in memory device 58 upon initial activation of energy delivery device 12.

Thereafter, to keep track of the total energy delivered to the human tissue, the total energy delivered is incremented in memory device 58 [230]. The temperature is monitored in a closed loop manner and a measure of the temperature at the treatment site is taken [235]. Main processor 25 determines the maximum temperature that has been attained during the use of energy delivery device 12 [240]. Main processor 25 also tracks the duration of time that energy delivery device 12 has been in use and increments the duration of the energy delivery [250]. Whether the treatment of the human tissue at that particular treatment site is completed can now be determined [265]. If the treatment at that treatment site is not finished, then the treatment process continues by incrementing the total energy delivery [230]. However, if the treatment at that particular treatment site is completed then the data and information from that treatment site is incrementally changed by main processor 25 based on the data and measurements taken at that location [270]. The usage-related parameters are then updated in memory device 58 [275]. Next, a determination is made as to whether the treatment by this medical treatment system 10 is completed [280]. If the treatment is not completed, then the treatment continues and treatment is initiated at another treatment site [225]. If the treatment of the human tissue is complete, then the treatment is ceased and the power to the energy delivery device 12 is turned off [285]. After the treatment has ceased, the medical personnel or other user may read the end of treatment parameters or other data from memory device 58 and may use this information for a number of purposes including the evaluation of the medical procedure itself.

Figure 9:
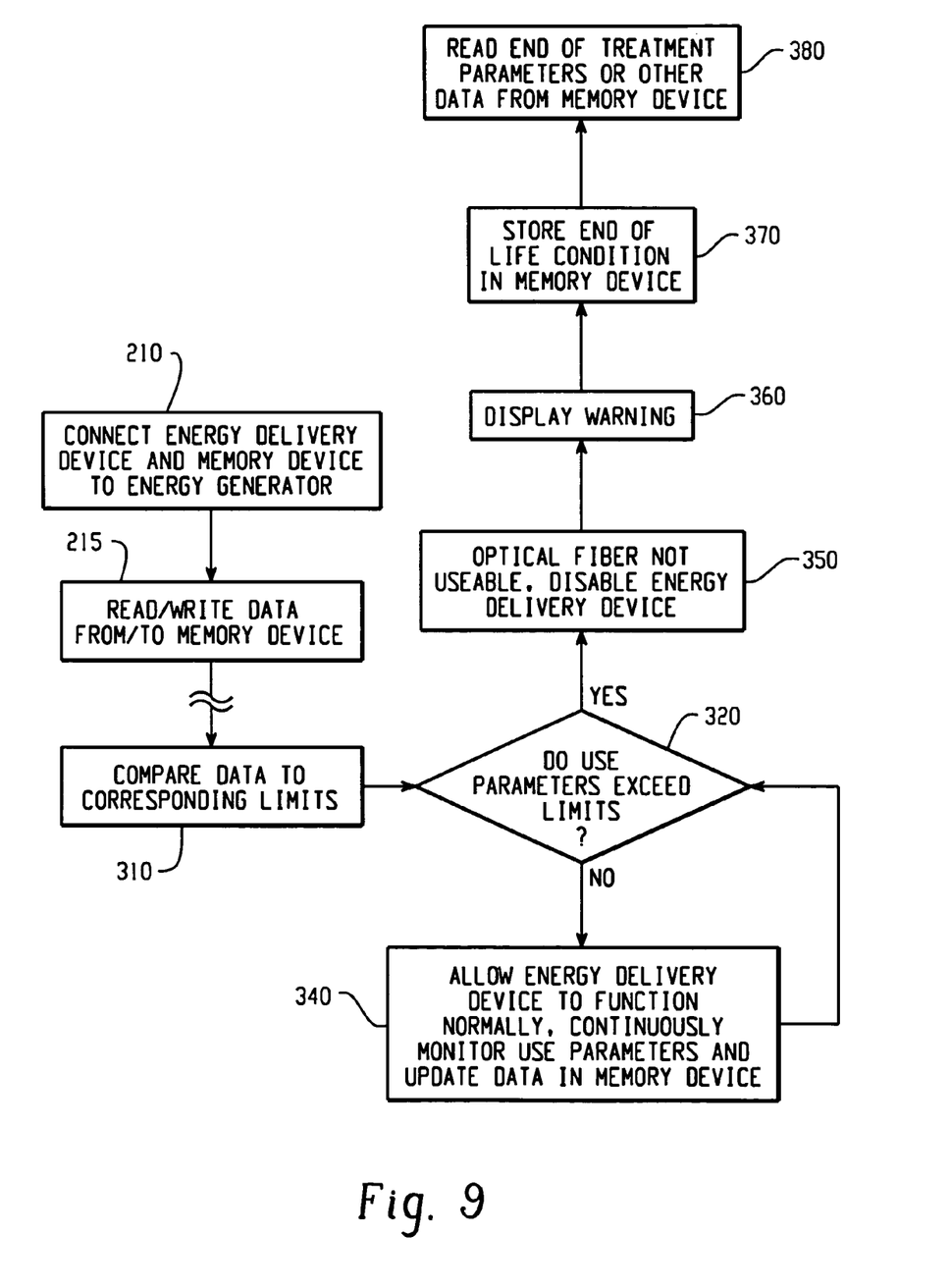
FIG. 9 is a flow chart illustrating a continuous process occuring in parallel with the method of FIG. 8.

While the above-identified steps are occuring, a particularly preferred method of limiting use of medical treatment system 10 shown in FIG. 9 is also being performed in parallel. In particular, the following steps occur on an on-going and continuous basis, simultaneous with the above identified process, after the energy delivery device 12 and memory device 58 has been operatively connected to the energy generator 22 [210], and after the data and information has been initially read from or written to the memory device [215]. Thereafter, the data and information including any usage-related parameters can be compared to its corresponding usage limits [310]. A determination regarding whether the particular use parameter exceeds its usage limit is also made [320]. If the particular usage limit has not been exceeded, then the energy delivery device 12 is allowed to function in its normal manner [340]. A portion of that normal manner of operation is to continuously monitor use parameters and update the data in memory device 58. If the use parameter has been exceeded, then optical fiber 13 is no longer useable and since energy delivery device 12 is not useable, the use thereof is disabled [350]. A warning can be displayed or enunciated to notify the user that the usage-related parameters exceed the predetermined limits [360]. Also, this end of life condition is stored in memory device 58 so that energy delivery device 12 will be permanently disabled to avoid future reuse the energy delivery device 12 while allowing users to read the data from memory device 58 regarding the condition of energy delivery device 12 [370]. The steps of disabling the energy delivery device 12, displaying a warning, and storing this information in memory device 58 can be preformed in any desired order or may even be performed simultaneously.

Thereafter, the user can read end of treatment parameters or other data from memory device 58 for purposes of evaluating the medical procedure or evaluating the energy delivery device 12 [380]. These use parameters as well as other data and information can be reviewed after completion of the medical procedure for trend tracking, historical verification, trouble shooting, problem resolution, analysis of error messages or reviewing performance of the energy delivery device 12 or any other portion of the medical treatment system 10 from which such data has been collected and stored in memory device 58. Standard report formats, individualized reports or even discrete data inquiries can be made to allow in depth analysis of the data. In addition to processing the data in numerous ways, additional steps can be provided without detracting from the primary purpose of the invention disclosed herein.

During normal operation of medical treatment system 10, light generated by energy generator 22 travels through core 31 to light-diffusing section 19. At light-diffusing section 19 the light energy emerges from core 31 through optical coupling layer 40 since optical coupling layer 40 has a higher index of refraction than core 31. The distal portion 44 of sleeve 38, which surrounds optical coupling layer 40, preferably uses barium sulfate particles scattered within sleeve 38 to diffuse the light energy evenly outwards towards the human tissue. Light energy reaching light-scattering component 48 is reflected back towards core 31 by the alexandrite particles in light-scattering component 48.

Such light-diffusing section 19 of optical fiber 13 of energy delivery device 12 is used to scatter and diffuse light into human tissue thereby heating the human tissue. It is preferable that light-diffusing section 19 emit energy into the human tissue in a substantially uniform manner. The energy is diffused radially outwardly in a uniform distribution along the entire length of light-diffusing section 19 to assure proper treatment of the human tissue.

After applying energy to the human tissue and completion of the medical procedure, the power is turned off and the user can then remove connector 28 from connector housing 36. To remove connector 28 the user simply rotates connector 28 from the locked position to the unlocked position. After rotating connector 28, the user can pull on handle portion 88 thereby easily removing connector 28 from energy generator 22.

The present invention thus provides an efficient medical treatment system 10 having ready capability for measurement of temperatures at the treatment location while providing limitations on reuse or overuse. This invention allows full consideration of a multiplicity of diverse factors when determining whether optical fiber 13 has reached an end of life condition. This invention also provides an energy delivery device 12 for use in such a system and a method for using the energy delivery device 12.

While preferred embodiments of the present invention have been shown and described herein, it will be understood by those skilled in the art that such embodiments are provided only by way of example. It can be seen by those skilled in the art that embodiments other than those illustrated can make use of the present invention. Numerous variations, modifications, changes, and substitutions may occur to those skilled in the art without departing from this invention. Accordingly, the invention is limited only by the appended claims hereto and the invention is entitled to protection within the full scope of such appended claims.

What is claimed is:

1. A method for limiting the use of an energy delivery device having an optical fiber and a memory device, said optical fiber includes a multiplicity of use parameters and at least one usage limit corresponding to at least one of said use parameters stored in said memory device and wherein said optical fiber further comprises a temperature sensor, said method comprising the steps of:

generating a temperature signal using said temperature sensor; and utilizing said temperature signal to determine whether at least one of said use parameters exceeds its corresponding usage limit; and disabling said energy delivery device when said use parameter exceeds said usage limit.

2. The method for limiting the use of an energy delivery device according to claim 1, wherein said optical fiber further includes a date of manufacture, further comprising the steps of:

storing said date of manufacture in said memory device; and utilizing said date of manufacture to determine whether said shelf life has expired.

3. The method for limiting the use of an energy delivery device according to claim 1, wherein said optical fiber further includes a shelf life, further comprising the steps of:

storing said shelf life in said memory device;

determining whether said shelf life has expired; and disabling said energy delivery device when said shelf life has expired.

4. A method for limiting the use of an energy delivery device having an optical fiber and a memory device wherein, said optical fiber includes a shelf life and a multiplicity of use parameters and a date of manufacture and at least one usage limit corresponding to at least one of said use parameters, said optical fiber further comprises a temperature sensor at a distal end thereof, said method comprising the steps of:

storing said shelf life in said memory device;

storing said use parameters and said usage limit in said memory device;

storing said date of manufacture in said memory device;

utilizing said date of manufacture to determine whether said shelf life has expired;

disabling said energy delivery device when said shelf life has expired determining whether at least one of said use parameters exceeds its corresponding usage limit;

generating a temperature signal using said temperature sensor; and utilizing said temperature signal to determine whether at least one of said use parameters exceeds its corresponding usage limit; and disabling said energy delivery device when said use parameter exceeds said usage limit.

5. A medical treatment system comprising:

an energy delivery device including an optical fiber and a memory device, said optical fiber including a temperature sensor at a distal end thereof for generating a temperature signal and said optical fiber having a predetermined usage limit, said usage limit stored in said memory device; and a processor programmed to calculate a temperature from said temperature signal and for utilizing said temperature signal in determining when said usage limit has been exceeded, said processor disabling the use of said energy delivery device when said usage limit has been exceeded.

6. The medical treatment system according to claim 5, further comprising a shelf life stored in said memory device and wherein said shelf life is between about 1 month to about 60 months.

7. The medical treatment system according to claim 5, wherein said optical fiber has a specified date of manufacture and wherein said date of manufacture is stored in said memory device.

8. The medical treatment system according to claim 5, wherein said optical fiber further includes a plurality of use parameters and a count limit and at least one usage limit corresponding to at least one of said use parameters all stored in said memory device.

9. The medical treatment system according to claim 8, wherein said processor updates said use parameters in response to a calculation by said processor and said processor compares said use parameters to a corresponding usage limit.

10. The medical treatment system according to claim 9, wherein said processor creates and increments a usage count when at least one of said use parameters exceeds its corresponding usage limit, and said processor compares said usage count to said count limit and disables use of said energy delivery device when said usage count exceeds said count limit.

11. A medical treatment system for performing a medical procedure comprising:

an energy delivery device including an optical fiber and a memory device, said optical fiber including a temperature sensor at a distal end thereof for generating a temperature signal, said optical fiber having a multiplicity of use parameters and a count limit and at least one usage limit corresponding to at least one of said multiplicity of use parameters relating to said optical fiber, said multiplicity of use parameters and said at least one usage limit and said count limit being stored in said memory device, and said optical fiber and said memory device being connected to said energy delivery device, and wherein said multiplicity of use parameters include at least an elapsed time, a total treatment time, and a number of treatment sites; and a processor programmed to calculate a temperature from said temperature signal, and said processor also programmed to update at least one of said multiplicity of use parameters in response to data received by said processor regarding said use parameter and said processor for comparing said use parameter to its corresponding usage limit, said processor creating and incrementing a usage count when at least one of said multiplicity of use parameters exceeds its usage limit, said processor comparing said usage count to said count limit and disabling said energy delivery device when said usage count exceeds said count limit.

12. The medical treatment system according to claim 11, wherein said optical fiber includes a predetermined shelf life and said shelf life is stored in said memory device.

13. The medical treatment system according to claim 12, wherein said processor determines when an actual date is beyond the expiration of said shelf life, and said processor disabling the use of said energy delivery device when said shelf life has expired.

14. The medical treatment system according to claim 13, wherein said at least one usage limit is an elapsed time limit, and wherein said elapsed time limit is between about one hour and about twelve hours.

15. The medical treatment system according to claim 12, wherein said shelf life is between about 1 month to about 60 months.

16. The medical treatment system according to claim 15, wherein said optical fiber has a primary count limit and a secondary count limit, said primary count limit and said secondary count limit being stored in said memory device, said processor comparing said usage count to said primary count limit and issuing a warning signal when said usage count exceeds said primary count limit and said processor comparing said usage count to said secondary count limit and disabling said energy delivery device when said usage count exceeds said secondary count limit.

17. The medical treatment system according to claim 12, wherein said optical fiber has a specified date of manufacture and said date of manufacture is stored in said memory device.

18. The medical treatment system according to claim 17, wherein said at least one usage limit further comprises a treatment time limit, and wherein said treatment time limit is about 36 minutes.

19. The medical treatment system according to claim 12, wherein said at least one usage limit further comprises a treatment site limit, and wherein said treatment site limit is about 12.

20. The medical treatment system according to claim 12, wherein data and information relating to the medical procedure or said medical treatment system can be read from said memory device after said energy delivery device has been disabled.

* * * * *

UNITED STATES PATENT AND TRADEMARK OFFICE
CERTIFICATE OF CORRECTION

| | | |
|---|---|---|
| PATENT NO. | : 7,118,564 B2 | Page 1 of 1 |
| APPLICATION NO. | : 10/723799 | |
| DATED | : October 10, 2006 | |
| INVENTOR(S) | : Paul G. Ritchie et al. | |

It is certified that error appears in the above-identified patent and that said Letters Patent is hereby corrected as shown below:

Title page, item (75) Inventors: add --Leo Samson, Pleasant Hill, CA (US)--.

Signed and Sealed this

Twelfth Day of December, 2006

JON W. DUDAS
*Director of the United States Patent and Trademark Office*